(12) United States Patent
Paatz et al.

(10) Patent No.: US 6,380,140 B1
(45) Date of Patent: Apr. 30, 2002

(54) ENZYME GRANULES CONTAINING PHOSPHATED STARCH

(75) Inventors: Kathleen Paatz; Wilfried Raehse, both of Duesseldorf; Werner Pichler, Kundl; Horst Upadek, Ratingen, all of (DE)

(73) Assignee: Henkel Komm.nditgesellschaft Auf Aktien, Duesseldorf (DE)

( * ) Notice: Subject to any disclaimer, the term of this patent is extended or adjusted under 35 U.S.C. 154(b) by 0 days.

(21) Appl. No.: 09/171,501

(22) PCT Filed: Apr. 12, 1997

(86) PCT No.: PCT/EP97/01836

§ 371 Date: Mar. 22, 1999

§ 102(e) Date: Mar. 22, 1999

(87) PCT Pub. No.: WO97/40128

PCT Pub. Date: Oct. 30, 1997

(30) Foreign Application Priority Data

Apr. 20, 1996 (DE) .......................... 196 15 776

(51) Int. Cl.$^7$ .......................... C11D 7/42; C12N 11/02; C12N 11/10; C12N 9/98; C12N 9/96
(52) U.S. Cl. .................. 510/108; 435/176; 435/177; 435/178; 435/179; 435/180; 435/187; 435/188; 510/392; 510/530
(58) Field of Search .................. 435/176, 177, 435/178, 179, 180, 182, 187, 188; 510/108, 226, 320, 392, 474, 530

(56) References Cited

U.S. PATENT DOCUMENTS

| | | | | |
|---|---|---|---|---|
| 3,034,911 A | * | 5/1962 | McKee et al. ............... | 106/210 |
| 3,623,956 A | | 11/1971 | Kalabokias ............... | 195/66 R |
| 3,784,476 A | | 1/1974 | van Kampen et al. ...... | 252/109 |
| 4,263,182 A | * | 4/1981 | Aldrich .......................... | 260/9 |
| 4,264,738 A | | 4/1981 | Stepanov et al. ........... | 435/222 |
| 4,704,416 A | * | 11/1987 | Eck et al. ..................... | 524/17 |
| 4,751,003 A | | 6/1988 | Raehse et al. .............. | 210/639 |
| 5,719,115 A | * | 2/1998 | Paatz et al. ................. | 510/392 |
| 5,846,798 A | * | 12/1998 | Paatz et al. ................. | 435/187 |
| 5,972,668 A | * | 10/1999 | Georg et al. ................ | 435/188 |

FOREIGN PATENT DOCUMENTS

| | | |
|---|---|---|
| CA | 923 069 | 3/1973 |
| CA | 974 907 | 9/1975 |
| CA | 2 146 063 | 10/1995 |
| DE | 16 17 188 | 2/1971 |
| DE | 16 17 190 | 2/1971 |
| DE | 16 17 232 | 2/1971 |
| DE | 19 40 488 | 2/1971 |
| DE | 20 44 161 | 4/1971 |
| DE | 17 67 568 | 7/1971 |
| DE | 21 01 803 | 7/1971 |
| DE | 20 32 768 | 1/1972 |
| DE | 21 21 397 | 11/1972 |
| DE | 18 03 099 | 2/1978 |
| DE | 21 37 042 | 3/1980 |
| DE | 21 37 043 | 5/1980 |
| DE | 29 25 427 | 1/1981 |
| DE | 40 41 752 | 6/1992 |
| DE | 43 10 506 | 10/1994 |
| EP | 0 006 638 | 1/1980 |
| EP | 0 168 526 | 1/1986 |
| EP | 0 170 360 | 2/1986 |
| EP | 0 200 032 | 11/1986 |
| EP | 0 564 476 | 4/1995 |
| GB | 1 263 765 | 2/1972 |
| GB | 1361387 | 7/1974 |
| JP | 57 165495 | 10/1982 |
| JP | 02 097388 | 4/1990 |
| WO | WO91/02792 | 3/1991 |
| WO | WO95/23221 | 8/1995 |
| WO | WO95/27049 | 10/1995 |
| WO | WO95/30010 | 11/1995 |
| WO | WO95/30011 | 11/1995 |
| WO | WO95/30743 | 11/1995 |
| WO | WO95/34627 | 12/1995 |

OTHER PUBLICATIONS

H.G. van Raay, et al., Tenside 7 (1970), pp. 125–132.

* cited by examiner

*Primary Examiner*—David M. Naff
(74) *Attorney, Agent, or Firm*—Glenn E. J. Murphy

(57) ABSTRACT

Enzyme granules suitable for incorporating into detergents or cleaners are provided containing an enzyme, a carrier material and a granulation auxiliary containing phosphated starch. The phosphated starch preferably has a mean degree of phosphation ranging from 1.5 to 2.5. Carrier materials include starch, cereal flour, cellulose, alkali metal aluminosilicate, layer silicate and alkali metal salts. Enzymes include proteases, lipases, amylases and cellulases. A preferred carrier material contains water-swellable starch, sucrose, cereal flour and cellulose powder. The granulation auxiliary may contain a co-granulation auxiliary selected from polyethylene glycol having an average molecular weight of from 200 to 6,000, 1,2-propylene glycol and a poly-ethoxylate having a specified formula. Preferred granules have a mean particle size of from 0.3 to 3 mm. The granules are produced by forming a mixture containing an aqueous enzyme-containing liquid such as a concentrated fermentation broth, the carrier material and the granulation auxiliary, extruding the mixture, cutting the extruded mixture to obtain granules, and optionally spheronizing and drying the granules.

18 Claims, No Drawings

ENZYME GRANULES CONTAINING PHOSPHATED STARCH

BACKGROUND OF THE INVENTION

1. Field of the Invention

This invention relates to enzyme granules, to a process for their production and to the use of the granules in solid, more particularly particulate detergents.

2. Discussion of Related Art

Enzymes, particularly proteases, are widely used in detergents, laundry aids and cleaning products. In general, the enzymes are used not in the form of concentrates, but in the form of mixtures with a diluent and carrier material. If enzyme preparations such as these are mixed with standard detergents, a considerable reduction in enzyme activity can occur during storage, particularly if bleaching-active compounds are present. Application of the enzymes to carrier salts accompanied by granulation in accordance with DE-OS 16 17 190 or by bonding with nonionic surfactants in accordance with DE-OS 16 17 188 or aqueous solutions of cellulose ethers in accordance with DE-OS 17 67 568 does produce a significant improvement in storage life because the sensitive enzymes in mixtures such as these are generally present on the surface of the carrier. Although the stability of the enzymes in storage can be significantly increased by encapsulating the enzymes with or embedding them in the carrier material and subsequently converting them into the desired particle form by extrusion, pressing and marumerizing as described for example in DE-PS 16 17 232, in DE-OS 20 32 768 and in DE-ASS 21 37 042 and 21 37 043, enzyme preparations of this type show unsatisfactory solubility properties The undissolved particles can become caught up in the washing and can soil it or can be discharged into the wastewater without being used. Although the encapsulating agents known from DE-OS 18 03 099, which consist of a mixture of solid acids or acidic salts and carbonates or bicarbonates and which disintegrate on addition of water, improve the solubility of enzyme preparations, they are extremely sensitive to moisture and, accordingly, require additional protective measures.

Another disadvantage of the preparation mentioned above is that the enzymes can only be processed in the form of dry powders. The fermenter broths typically formed in the production of the enzyme preparations cannot be used in this form, but instead have to be freed from water beforehand. The same is also a precondition in processes where only readily soluble carrier materials, such as sugars, starch and cellulose ethers, are used as binders in the production of enzyme preparations.

EP 168 526 describes enzyme granules containing starch swellable in water, zeolite and water-soluble granulation aids. This document discloses a process for the production of such formulations which essentially comprises concentrating a fermenter solution freed from insoluble constituents, introducing the additives mentioned and granulating the resulting mixture. The process with the proposed additive mixture is advantageously carried out with fermentation solutions which have been concentrated to a relatively high dry matter content, for example of 55% by weight. In addition, the granules thus produced are highly soluble and disintegrate rapidly under washing conditions so that the granules disintegrate relatively quickly, to some extent even in storage, and the enzymes are deactivated.

European patent EP 0 564 476 describes enzyme granules for use in granular detergents which contain 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. Additives such as these enable the enzymes to be processed without significant losses of activity. The storage stability of the enzymes in the granules is also satisfactory. It is also known from this document that sodium carboxymethyl cellulose reduces the disintegration and dispersion rate of the granules in cold wash liquors whereas the addition of relatively high molecular weight polyethylene glycol can vary this effect by increasing the dissolving rate. However, the enzyme granules described in the document in question do not always have such a high disintegration rate that, where they are used in detergents, enough enzyme is present in the wash liquor to eliminate enzymatically removable soils even in the initial phase of machine washing. The use of a special granulation auxiliary system containing alkali metal carboxymethyl cellulose with degrees of substitution of 0.5 to 1 and polyethylene glycol and/or alkyl or alkenyl polyethoxylate in certain quantities was proposed in German patent application DE 43 10 506 as the starting point for a further improvement in solubility. Enzyme granules produced using this granulation auxiliary system do not provide an entirely satisfactory solution to the problem of dispensing behavior in domestic washing machines where the dispensing compartment is not optimally shaped or positioned.

The problem addressed by the present invention was further to develop the attempt to solve these problems through the granulation aid and further to improve the powder properties, more particularly the solubility and dispensing behavior of known products, further to increase the stability in storage both of the enzymes and of the granules containing them and further to reduce losses of activity during processing of the enzymes. According to the invention, this problem has largely been solved by a special granulation auxiliary system.

SUMMARY OF THE INVENTION

The present invention relates to enzyme granules suitable for incorporation in detergents, particularly particulate detergents, containing enzyme and inorganic and/or organic carrier material and granulation auxiliary, characterized in that they contain a phosphated, optionally partly hydrolyzed starch as the granulation auxiliary. In the context of the invention, phosphated starch is understood to be a starch derivative in which the hydroxyl groups of the starch anhydroglucose units are replaced by the group —O—P(O)(OH)$_2$ or water-soluble salts thereof, more particularly alkali metal salts, such as sodium and/or potassium salts.

In the context of the invention, the mean degree of phosphation of the starch is understood to be the number of esterified oxygen atoms bearing a phosphate group per saccharide monomer of the starch averaged over all the saccharide units. The mean degree of phosphation of the phosphated starches preferably used is in the range from 1.5 to 2.5 because, where these starches are used, much smaller quantities are required to achieve a certain granule strength than where carboxymethyl cellulose is used. Partly hydrolyzed starches in the context of the present invention are understood to be oligomers or polymers of carbohydrates which may be obtained by partial hydrolysis of starch using conventional methods, for example acid- or enzyme-catalyzed methods. They are preferably hydrolysis products with average molecular weights of 440 to 500,000. Polysaccharides having a dextrose equivalent (DE) of 0.5 to 40 and, more particularly, in the range from 2 to 30 are preferred.

The dextrose equivalent (DE) is a standard measure of the reducing effect of a polysaccharide by comparison with dextrose which has a DE of 100. Both maltodextrins (DE 3–20) and dry glucose sirups (DE 20–37) and so-called yellow dextrins and white dextrins with relatively high average molecular weights of about 2,000 to 30,000 are also suitable after phosphation.

DETAILED DESCRIPTION OF THE INVENTION

In one preferred embodiment, the enzyme granules contain 0.01% by weight to 25% by weight and, more particularly, 4% by weight to 20% by weight, expressed as dry matter, of enzyme, more particularly protease, lipase, amylase and/or cellulase, 50% by weight to 90% by weight of inorganic and/or organic carrier material and 1% by weight to 50% by weight of granulation auxiliary system containing the phosphated starch, the balance to 100% by weight being water.

Enzyme granules according to the invention preferably contain a mixture containing—based on the final granules—0.1% by weight to 20% by weight and, more particularly, 0.5% by weight to 15% by weight of phosphated starch and 0.1% by weight to 15% by weight and, more particularly, 0.5% by weight to 10% by weight of polyethylene glycol with an average molecular weight of 200 to 6,000, 1,2-propylene glycol and/or a polyethoxylate corresponding to formula I

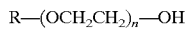   I where R is a linear or branched alkyl or alkenyl group containing up to 3 C—C double bonds and 8 to 22 and, more particularly, 12 to 18 carbon atoms and the average degree of ethoxylation n is a number of 10 to 80 and, more particularly, 30 to 45, as the granulation auxiliary system.

The present invention also relates to a process for the production of the enzyme granules with a particle size of 0.3 mm to 3 mm by extruding an enzyme "compound" prepared by mixing an aqueous enzyme-containing liquid, which may be a concentrated fermentation broth optionally freed from insoluble constituents by microfiltration, with the carrier material and the granulation auxiliary as additives, optionally spheronizing the extrudate in a spheronizer, optionally drying and optionally applying a dye- or pigment-containing coating, characterized in that the aqueous enzyme-containing liquid is mixed with an additive which contains phosphated starch or a granulation auxiliary system of phosphated starch and polyethylene glycol and/or polyethoxylate corresponding to formula I as the granulation auxiliary.

Suitable enzymes are, above all, the proteases, lipases, amylases and/or cellulases obtained from microorganisms, such as bacteria or fungi, proteases produced by bacillus species and mixtures thereof with amylases being preferred. They are obtained in known manner by fermentation processes from suitable microorganisms which are described, for example, in DE-OSS 19 40 488, 20 44 161, 21 01 803, and 21 21 397, in U.S. Pat. Nos. 3,623,956 and 4,264,738 and in European patent application EP 006 638. The process according to the invention may be used with particular advantage for formulating highly active so-called fourth generation proteases including, for example, Durazym® and enzymes known from International patent applications WO 95/23221, WO 95/27049, WO 95/30010, WO 95/30011, WO 95/30743 or WO 95/34627, of which the storage-stable incorporation in detergents is generally problematical.

According to the invention, the broths of extracellular enzymes accumulating in the fermentation processes may be directly converted into storable, substantially odorless granules after separation of the insoluble constituents by microfiltration and subsequent concentration by ultrafiltration and, optionally, subsequent concentration by evaporation in vacuo. The formation of unwanted enzyme dusts and the losses of activity occurring in additional drying processes are avoided.

Enzymes are preferably present in the granules according to the invention in quantities of 0.01% by weight to 20% by weight. If the enzyme granules according to the invention are based on a protease-containing formulation, the protease activity is preferably 60,000 protease units (PU, as determined by the method described in Tenside 7 (1970), 125) to 350,000 PU and, more preferably, 140,000 PU to 280,000 PU per gram of enzyme granules.

In principle, suitable carrier materials are any organic or inorganic powders which destroy or deactivate the enzymes to be granulated only negligibly, if at all, and which are stable under granulation conditions. Powder-form substances such as these include, for example, starch, cereal flour, cellulose powder, alkali metal alumosilicate, more particularly zeolite, layer silicate, for example bentonite or smectite, and water-soluble inorganic or organic salts, for example alkali metal chloride, alkali metal sulfate, alkali metal carbonate or alkali metal acetate, sodium or potassium being the preferred alkali metals. A carrier mixture of water-swellable starch, cellulose powder and optionally alkali metal carbonate is preferably used.

The starch swellable in water is preferably corn starch, rice starch potato starch or mixtures thereof, corn starch being particularly preferred. Swellable starch is present in the enzyme granules according to the invention in quantities of, preferably, 20% by weight to 70% by weight and, more preferably, 25% by weight to 60% by weight, the sum total of the quantities of swellable starch and flour preferably being no more than 80% by weight and, more particularly, between 32% by weight and 70% by weight.

The cereal flour suitable for use in accordance with the invention, which can contribute towards reducing the odor of the enzyme granules, is in particular a product obtainable from wheat, barley, rye or oats or a mixture of such flours, whole grain flours being preferred. In the context of the invention, a whole grain flour is understood to be a flour which has not been fully ground and which has been produced from whole unshelled grains or which consists at least predominantly of such a product, the remainder consisting of fully ground flour or starch. Commercial wheat flours, for example Type 450 or Type 550, are preferably used. It is also possible to use flours of the cereals leading to the swellable starches mentioned above providing the flours have been produced from the whole grains. The cereal flour may be present in the enzyme granules according to the invention in quantities of, preferably, 10% by weight, to 35% by weight and, more preferably, 15% by weight to 25% by weight. However, since it has now surprisingly been found that phosphated starch tends to reduce the odor of the enzyme preparation to a greater extent than cereal flour, the flour component of the additive mixture can be omitted altogether. If desired, the storage stability of the enzymes and their granulation behavior in the production process can be improved by the use of cereal flour proteins, such as gluten, which can be obtained by extraction of the non-protein-containing constituents of the flour.

The enzyme granules according to the invention preferably contain 1% by weight to 50% by weight and, more preferably, 3% by weight to 25% by weight of the granulation auxiliary or granulation auxiliary system containing phosphated starch and, optionally, polyethylene glycol, 1,2-propylene glycol and/or alkyl polyethoxylate. This granulation auxiliary system preferably contains—based on the final enzyme granules—1% by weight to 15% by weight and, more particularly, 3% by weight to 10% by weight of phosphated starch and up to 5% by weight and, more particularly, 0.5% by weight to 3% by weight of polyethylene glycol, 1,2-propylene glycol and/or polyethoxylate corresponding to formula I. Alkali metal carboxymethyl cellulose, more particularly carboxymethyl cellulose with degrees of substitution of up to 3, is preferably not present in the granulation auxiliary system according to the invention.

Optional additional constituents of the granulation auxiliary system include other cellulose or starch ethers, such as carboxymethyl starch, methyl cellulose, hydroxyethyl cellulose, hydroxypropyl cellulose and corresponding cellulose mixed ethers, gelatine, casein, the above-mentioned cereal flour protein, tragacanth, maltodextrose, sucrose, invert sugar, glucose sirup or other water-soluble or water-dispersible oligomers or polymers of natural or synthetic origin. Suitable synthetic water-soluble polymers are polyacrylates, polymethacrylates, copolymers of acrylic acid with maleic acid or compounds containing vinyl groups, polyvinyl alcohol, partially hydrolyzed polyvinyl acetate and polyvinyl pyrrolidone. If the compounds mentioned above are those containing free carboxyl groups, they are normally present in the form of their alkali metal salts, more particularly their sodium salts. Additional granulation auxiliaries such as these may be present in the enzyme granules according to the invention in quantities of up to 15% by weight and, more particularly, in quantities of 0.5% by weight to 10% by weight.

In one preferred embodiment of enzyme granules according to the invention or produced by the process according to the invention, the carrier material contains—based on the final enzyme granules—10% by weight to 70% by weight of water-swellable starch, 3% by weight to 10% by weight of sucrose, up to 70% by weight and, more particularly, 10% by weight to 70% by weight of cereal flour and up to 10% by weight of cellulose powder.

The enzyme granules according to the invention are preferably produced from fermenter broths which may be freed from insoluble constituents by microfiltration. The microfiltration process is preferably carried out as crossflow microfiltration using porous tubes with micropores larger than 0.1 μm, flow rates of the concentrate solution of more than 2 m/s and a pressure difference relative to the permeate side of less than 5 bar, as described for example in European patent application EP 200 032. The microfiltration permeate is then concentrated, preferably by ultrafiltration optionally followed by evaporation in vacuo. As described in European patent EP 0 564 476 the concentration phase can be carried out in such a way that only relatively low dry matter contents of preferably 5% by weight to 50% by weight and, more preferably, 10% by weight to 40% by weight are obtained. The concentrate is added to a dry powder-form to granular mixture of the additives described above which is best prepared beforehand. The water content of the mixture should be selected so that it can be converted into granular particles which are non-tacky at room temperature by treatment with stirring and beating tools and can be plastically deformed and extruded by application of relatively high pressures. In a preferred embodiment, 10 parts by weight to 50 parts by weight of the concentrated fermenter broth are mixed with 70 parts by weight to 90 parts by weight of the carrier material and 0.5 part by weight to 10 parts by weight of the granulation auxiliary or granulation auxiliary system.

The free-flowing compound is then processed in a kneader and an adjoining extruder in basically known manner to form a plastic mass which can assume temperatures of 40° C. to 60° C. and, more particularly, 45° to 55° C. as a result of the mechanical treatment. The material leaving the extruder passes through a multiple-bore extrusion die followed by a cutting blade so that it is size-reduced to cylindrical particles of defined size. The diameter of the bores in the multiple-bore extrusion die is 0.3 mm to 3 mm and preferably 0.5 mm to 1.5 mm. The particles present in this form may then be dried and put to their intended use. However, it has proved to be of advantage subsequently to spheronize the cylindrical particles leaving the extruder and cutter, i.e. to round off and deflash the particles in suitable units. One such spheronizing process is described, for example, in DE-ASS 21 37 042 and 21 37 043. An arrangement consisting of a cylindrical container with fixed side walls and a friction plate rotatably mounted at its base is used for this purpose. Machines of this type are commercially available under the name of Marumerizer®.

After the spheronizing step, the beads which are still moist are dried continuously or in batches to a residual moisture content of 4% by weight to 10% by weight and preferably 5% by weight to 8% by weight at a maximum product temperature of preferably 35° C. to 60° C. and, more particularly, 45° C., preferably using a fluidized-bed dryer. Substances for encapsulating and coating the particles may be additionally introduced after or preferably during the drying step. Suitable encapsulating materials are, in particular, the film formers among the water-soluble organic polymers mentioned above. In addition, dyes or pigments may also be applied to the particles at this stage in order to mask or modify any color which may be present—generally from the enzyme concentrate. Titanium dioxide in particular has proved to be an inert and physiologically safe pigment and is preferably introduced in the form of an aqueous dispersion. The water introduced through the pigment dispersion or through the polymer solution is removed again during the drying step carried out at the same time or repeated thereafter.

The enzyme granules according to the invention or produced by the process according to the invention are preferably used for the production of solid, more particularly particulate, detergents or cleaning products which may be obtained simply by mixing the enzyme granules with other powder components typically used in such compositions. For incorporation in particulate detergents, the enzyme granules preferably have mean particle sizes of 0.3 mm to 3 mm and, more particularly, in the range from 0.5 mm to 1.5 mm.

Any dust-fine particles and any coarse particles occurring during production may be removed by sieving or air separation and optionally returned to the production process. The granules according to the invention preferably contain less than 5% by weight and, more particularly, at most 1% by weight of particles with particle sizes below 0.3 mm and above 1.6 mm.

The enzyme preparation obtained consists of largely rounded dust-free particles which generally have a bulk density of about 500 to 900 grams per liter and, more particularly, in the range from 650 to 880 grams per liter. Where protease-containing fermenter broths are used, their enzyme activity can be adjusted to values of preferably 60,000 to 350,000 protease units per gram (PU/g) and, more preferably, 140,000 PU/g to 280,000 PU/g by virtue of the flexible dry matter content of the broths before mixing with the additives. The granules according to the invention are distinguished by very high stability in storage, more particularly at temperatures above room temperature and in atmospheres of high humidity, by favorable dispensing behavior in washing machines and by rapid solubility in the wash liquor. The granules according to the invention preferably develop 90% to 100% of their enzyme activity within 5 minutes in water at 30° C. A sign of their favorable dispensing behavior is that, when dissolved in a quantity of 8 g in 2,000 ml of water at 30° C., enzyme granules according to the invention or produced in accordance with the invention preferably have a sieve residue (0.2 mm mesh sieve) of less than 3% by weight and, more particularly, less than 1.5% by weight after 90 seconds, as described below.

EXAMPLES

Example 1

A biomass-containing fermenter broth containing around 65,000 protease units per gram (PU/g) was obtained by fermentation of Bacillus licheniformis (ATCC 53926)—modified by the process described in International patent application WO 91/02792 by transformation of a gene sequence from Bacillus lentus DSM 5483—by the process described in DE-PS 29 25 427. The fermenter broth was concentrated to a protease content of 700,000 PU/g by decantation, crossflow microfiltration, ultrafiltration (cutoff limit at molecular weight 10,000) and subsequent concentration by evaporation in vacuo in accordance with European patent EP 0 564 476 (B1). The fermenter broth thus concentrated was mixed with the additives listed in Table 1 in a mixer equipped with a rotating beating tool and homogenized in a kneader provided with external cooling. The plastic compound was extruded in an extruder equipped with a multiple-bore extrusion die (bore diameter 0.9 mm) and a rotating blade. The 0.7 mm to 1 mm long extrudates x1 to x7 according to the invention and comparison extrudates C1 to C4 characterized by their composition in Table 1 were obtained and were converted into spherical particles and deflashed in a spheronizer (Marumerizer) over a period of about 1 minute during which they were dusted with powder-form calcium carbonate (3% by weight). The material leaving the spheronizer was dried for 15 minutes at 40 to 45° C. in a fluidized-bed dryer to a water content of 6% by weight. Particles smaller than 0.4 mm and larger than 1.6 mm in size were largely removed by subsequent sieving and were returned to the process at the stage comprising mixing with the additives. The enzyme granules were coated by spraying with an aqueous titanium dioxide pigment suspension during fluidized-bed drying. Enzyme granules P1 to P7 according to the invention and comparison granules CG1 to CG4 with the dissolving times and residue values shown in Table 2 were thus obtained.

TABLE 1

| Enzyme extrudates | | | | | | | | | | | |
|---|---|---|---|---|---|---|---|---|---|---|---|
| | X1 | X2 | X3 | X4 | X5 | X6 | X7 | C1 | C2 | C3 | C4 |
| B1 | 26 | 26 | 22 | 22 | 24 | 24 | 22 | 27 | 27 | 27 | 27 |
| Cellulose powder[a] | 3 | 3 | 3 | 3 | 3 | 3 | 3 | 3 | 3 | 3 | 3 |
| Sucrose | 6 | 6 | 6 | 6 | 6 | 6 | 6 | 6 | 6 | 6 | 6 |
| Wheat flour T 450 | 16 | 16 | 16 | 16 | 16 | — | — | 14 | 16 | 16 | 16 |
| Corn starch | 43 | 44 | 46 | 46 | 42 | 57 | 58 | 43 | 43 | 43 | 43 |

TABLE 1-continued

| Enzyme extrudates | | | | | | | | | | | |
|---|---|---|---|---|---|---|---|---|---|---|---|
| | X1 | X2 | X3 | X4 | X5 | X6 | X7 | C1 | C2 | C3 | C4 |
| Phosphated starch[b] | 4 | 3 | 4 | 4 | 6 | 7 | 4 | — | — | — | — |
| Gluten[c] | — | — | — | — | — | — | 4 | — | — | — | — |
| CMC-I[d] | — | — | — | — | — | — | — | — | — | — | 3 |
| CMC-II[e] | — | — | — | — | — | — | — | 5 | 3 | 3 | — |
| PEG-I[f] | — | — | — | — | — | — | — | — | — | 2 | 2 |
| PEG-II[g] | 2 | 2 | 3 | — | 3 | 3 | 3 | 2 | 2 | — | — |
| Surfactants[h] | — | — | 3 | — | — | — | — | — | — | — | — |

[a]Technocel ® 30 (a product of Cellulose Füllstoff Fabrik)
[b]Pregeflo ® PJ 20 (mean degree of phosphation 2; a product of Roquette-Frere)
[c]Devital ® wheat adhesive (a product of Roquette-Frere)
[d]Carbocel ® 300 (degree of substitution 0.65–0.75; a product of Lamberti CMC)
[e]Carbocel ® 500 (degree of substitution 0.85–0.95; a product of Lamberti CMC)
[f]Polyethylene glycol, average molecular weight 400
[g]Polyethylene glycol, average molecular weight 2,000
[h]40x ethoxylated tallow fatty alcohol (a product of Henkel KGaA)

Example 2

To determine the residue value, 1,000 ml of water (temperature 30° C., hardness 16° dH) were poured into a 2,000 ml glass beaker (tall form), a laboratory stirrer with a propeller stirrer head was fixed centrally 1.5 cm from the bottom of the glass beaker and was set in motion at 800 r.p.m. 8 g of the granules to be tested were scattered in and stirred for 90 seconds. The liquid in the glass beaker was then poured through a sieve (mesh width 0.2 mm) of known weight, the glass beaker was rinsed with a little cold water and the sieve was weighed after drying at 40° C. to constant weight. The sieve residues (double determination) shown in Table 2 were obtained.

TABLE 2

Sieve residues of the enzyme granules

| Enzyme granules | Sieve residue [% by weight] |
|---|---|
| P1 | 0.6 |
| P2 | 0.1 |
| P3 | 0.1 |
| P4 | 0.2 |
| P5 | 0.1 |
| P6 | 0.8 |
| P7 | 1.2 |
| CG1 | 41 |
| CG2 | 23 |
| CG3 | 36 |
| CG4 | 17 |

Example 3

The enzyme granules according to the invention and the enzyme granules produced for comparison from Example 1 were dissolved under standardized conditions as described in European patent EP 0 564 476. The enzyme activities in the solution shown in Table 3 in percent of the final value (=no further change as a function of time) were obtained after stirring for 5 minutes at 30° C.

TABLE 3

Enzyme activity after 5 minutes

| Enzyme granules | Activity [%] |
|---|---|
| P1 | 96 |
| P2 | 95 |
| P3 | 100 |
| P4 | 100 |
| P5 | 100 |
| P6 | 98 |
| P7 | 100 |
| CG1 | 82 |
| CG2 | 88 |
| CG3 | 85 |
| CG4 | 93 |

What is claimed is:

1. An enzyme granule composition comprising:
   (a) 0.01% to 20% by weight of an enzyme component;
   (b) 50% to 90% by weight of a carrier material comprising a substance selected from the group consisting of starch, cereal flour, cellulose, alkali metal aluminosilicate, layer silicate, and mixtures thereof; and
   (c) 1% to 50% by weight of a granulation auxiliary comprising a phosphated starch, wherein the phosphated starch comprises 0.1% to 20% by weight of the granule composition.

2. The composition of claim 1 wherein the phosphated starch has a mean degree of phosphation ranging from 1.5 to 2.5.

3. The composition of claim 1 wherein the granulation auxiliary further comprises from 0.1 to 15% by weight of a co-granulation auxiliary selected from the group consisting of a polyethylene glycol having an average molecular weight of from 200 to 6,000, 1,2-propylene glycol, a poly-ethoxylate corresponding to the formula (I):

$$R-(OCH_2CH_2)_n-OH \qquad (I)$$

wherein R is a linear or branched alkyl or alkenyl group containing up to 3 C=C double bonds and from 8 to 22 carbon atoms and n is a number from 10 to 80, and mixtures thereof, all weights being based on the weight of the composition.

4. The composition of claim 1 wherein the granulation auxiliary further comprises up to 15% by weight of a water-soluble or water-dispersable oligomer or polymer of natural or synthetic origin.

5. The composition of claim 1 wherein the carrier material comprises from 20 to 70% by weight of water-swellable starch.

6. The composition of claim 3 wherein the water-swellable starch is corn starch.

7. The composition of claim 1 wherein the enzyme component is selected from the group consisting of a protease, a lipase, an amylase, a cellulase and mixtures thereof.

8. The composition of claim 1 wherein a plurality of enzyme granules having the composition are present and the enzyme granules have a mean particle size of from 0.3 to 3 mm, and wherein less than 5% by weight of the enzyme granules are below 0.3 mm in size, and wherein less than 5% by weight of the enzyme granules are greater than 1.6 mm in size.

9. The composition of claim 1 wherein at least 90% of the enzyme component is released upon contact with water at 30° C. within 5 minutes.

10. The composition of claim 1 wherein the enzyme granules, when dissolved in quantities of 8 grams in 2,000 ml of water at 30° C., have a sieve residue after 90 seconds of less than 3% by weight.

11. A powdered cleaning composition containing the enzyme granule composition of claim 1.

12. A process for making enzyme granules having a mean particle size of from 0.3 to 3 mm comprising:
   (a) providing an aqueous enzyme composition containing:
      (i) a concentrated enzyme-containing fermentation broth;
      (ii) a carrier material; and
      (iii) a granulation auxiliary comprising a phosphated starch; and
   (b) extruding the aqueous enzyme composition enzyme through an extrusion die having a 0.3 to 3. m diameter bore followed by cutting the extruded composition to obtain the granules having a mean particle size of from 0.3 to 3 mm, wherein said granules comprise 0.01% to 20% by weight of an enzyme component derived from the fermentation broth, 50% to 90% by weight of the carrier material, which comprises a substance selected from the group consisting of starch, cereal flour, cellulose, alkali metal aluminosilicate, layer silicate, and mixtures thereof, and 1% to 50% by weight of the granulation auxiliary comprising a phosphated starch, wherein the phosphated starch comprises 0.1% to 20% by weight of the granule.

13. The process of claim 12 further comprising spheronizing the enzyme granules.

14. The process of claim 12 further comprising drying the enzyme granules to a residual moisture content of from 4 to 10% by weight.

15. The process of claim 12 wherein the aqueous enzyme composition contains:
   (i) from 10 to 50 parts by weight of the concentrated enzyme-containing fermentation broth;
   (ii) from 70 to 90 parts by weight of the carrier material; and
   (iii) from 0.5 to 10 parts by weight of the granulation auxiliary, all weights being based on the weight of the aqueous enzyme composition.

16. The process of claim 12 wherein the granulation auxiliary further comprises a co-granulation auxiliary selected from the group consisting of a polyethylene glycol having an average molecular weight of from 200 to 6,000, 1,2-propylene glycol, a poly-ethoxylate corresponding to the formula (I):

$$R-(OCH_2CH_2)_n-OH \qquad (I)$$

wherein R is a linear or branched alkyl or alkenyl group containing up to 3 C=C double bonds and from 8 to 22 carbon atoms and n is a number from 10 to 80, and mixtures thereof, all weights being based on the weight of the composition.

17. The process of claim 12 wherein the carrier material comprises:
   (a) from 10 to 70% by weight of a water-swellable starch;
   (b) from 3 to 10% by weight of sucrose;
   (c) up to 70% by weight of cereal flour; and
   (d) up to 10% by weight of cellulose powder, all weights being based on the weight of the carrier material.

18. The process of claim 12 wherein the phosphated starch has a mean degree of phosphation of from 1.5 to 2.5.

* * * * *

UNITED STATES PATENT AND TRADEMARK OFFICE
CERTIFICATE OF CORRECTION

PATENT NO. : 6,380,140 B1
DATED : April 30, 2002
INVENTOR(S) : Paatz et al.

It is certified that error appears in the above-identified patent and that said Letters Patent is hereby corrected as shown below:

<u>Title page,</u>
Item [73], Assignee, delete "Komm.nditgesellschaft", and insert therefor
-- Kommanditgesellschaft --.

<u>Column 10,</u>
Line 14, after "3.", delete "m", and insert therefor -- mm --.

Signed and Sealed this

Eighth Day of July, 2003

JAMES E. ROGAN
*Director of the United States Patent and Trademark Office*